United States Patent [19]

Ternansky

[11] Patent Number: 5,116,972

[45] Date of Patent: May 26, 1992

[54] 4-(2,3 EPOXYPROPANE)AZETIDINONES

[75] Inventor: Robert J. Ternansky, Indianapolis, Ind.

[73] Assignee: Eli Lilly and Company, Indianapolis, Ind.

[21] Appl. No.: 744,857

[22] Filed: Aug. 14, 1991

Related U.S. Application Data

[62] Division of Ser. No. 691,257, Apr. 25, 1991, Pat. No. 5,089,610.

[51] Int. Cl.$^5$ ............... C07D 405/06; C07D 7/10; C07D 205/095; C07D 205/085
[52] U.S. Cl. ................... 540/364; 540/205; 540/359
[58] Field of Search ............... 540/364

[56] References Cited

U.S. PATENT DOCUMENTS 4,983,732  1/1991  Blaszczak ............... 540/360

OTHER PUBLICATIONS

Astleford, Chem. Abs. 115, 114208x (1991, Jul.) with attached structure.
Achini and Oppolzer, Tetrahedron Letters, No. 6, 369-372 (1975), "Synthesis of Pyrrolidines by Intramolecular Carbanionic Epoxide Opening".

*Primary Examiner*—Mark L. Berch
*Attorney, Agent, or Firm*—James J. Sales; Leroy Whitaker

[57] ABSTRACT

The invention provides novel compounds of the formula

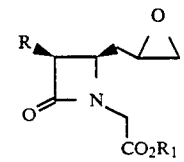

wherein R is a protected amino group and R1 is a carboxy protected group.

2 Claims, No Drawings

4-(2,3 EPOXYPROPANE)AZETIDINONES

This application is a division of application Ser. No. 07/691,257, filed Apr. 25, 1991, now U.S. Pat. No. 5,089,610.

FIELD OF THE INVENTION

This invention is related to a process for the preparation of 1-carba(1-dethia)-3-cephem-4-carboxylic acids and derivatives thereof, and more particularly to a ring closure method of the six-membered ring of 1-carba(1-dethia)-3-cephem-4-carboxylic acids from 3-protected amino-4-alkenyl azetidinones and intermediates.

BACKGROUND OF THE INVENTION

The 1-carba(1-dethia)-3-cephem-4-carboxylic acids, hereinafter 1-carbacephalosporins, or carbacephs, possess the 4,6-bicyclic ring system represented by the following structural formula

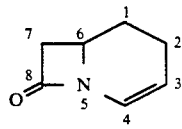

wherein the arbitrary numbering system employed according to the cepham nomenclature is used for convenience as indicated.

1-Carbacephalosporin compounds provide significant synthetic challenges. The 1-carbacephalosporins thus far have not been obtained from natural sources, for example, as microbial metabolites. Accordingly, methods for the total synthesis of these promising compounds are highly desirable, particularly methods which are adaptable to large scale manufacture. One of the more noteworthy approaches to total synthesis of 1-carbacephalosporins is the asymmetric route described by Evans, et al., U.S. Pat. No. 4,665,171.

One further route to cis-chiral azetidinones with regularly derivatized 4-allyl (and substituted allyl) groups, is provided by Blaszczak, U.S. Pat. No. 4,771,134. The Blaszczak method utilizes 4-(substituted selenyl) azetidinones as starting materials which are converted to 4-allyl(and substituted allyl) azetidinones under free radical conditions using a (2-substituted or unsubstituted allyl) tin agent.

The preparation of 1-carbacephalosporanic acids and C-3 substituted methyl derivatives thereof is taught broadly by Christensen et al., U.S. Pat. No. 4,226,866. Hirata et al., U.K. Patent Application No. 2041923 teach a process for preparing 3-halo and 3-H 1-carbacephalosporins; and Hatanaka et al., *Tetrahedron Letters*, Vol. 24, No. 44, pp 4837–4838 (1983), teach a process for preparing a 3-hydroxy-(+/−)-1-carbacephalosporin.

SUMMARY

A process for preparing 1-carbacephalosporins which includes the steps of subjecting a 3-protected amino-4-(1-propyleneoxide)-1-methyl(protected carboxy)-azetidin-2-one compound to a strong base and thereafter dehydrating the resultant product to provide a 7-protected amino-4-protected carboxy-1-carbacephalosporin.

DETAILED DESCRIPTION

The present invention provides a process for preparing compounds of the formula (IV)

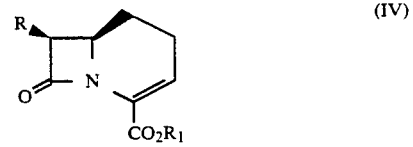

wherein R is a protected-amino group and $R_1$ is a carboxy-protecting group by reacting a compound of formula (II)

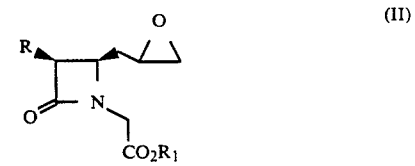

with a strong base under substantially anhydrous conditions in the presence of an inert organic solvent for a time and at a temperature sufficient to form a compound of the formula (III)

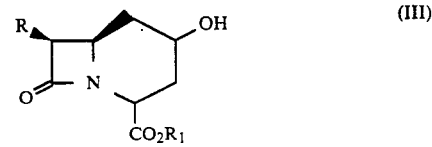

and thereafter dehydrating the compound of formula (III) to form a compound of formula (IV).

In the above process, the term "protected-amino group" refers to an amino group substituted by groups commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl, iodoacetyl, phenoxyacetyl and phenylacetyl groups, urethane-type blocking groups such as benzyloxycarbonyl, allyloxycarbonyl 4-phenylbenzyloxycarbonyl, 2-methylbenzyloxycarbonyl, 4-methoxybenzyloxycarbonyl, 4-fluorobenzyloxycarbonyl, 4-chloro-benzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromo-benzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-xyloxycarbonyl, 2-(p-toluyl)prop-2-yloxycarbonyl, cyclopentyloxycarbonyl, 1-methylcyclopentyloxycarbonyl, cyclohexyloxycarbonyl, 1-methylcyclohexyloxycarbonyl, 2-methylcyclohexyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobornyloxycarbonyl, 1-piperidyloxycarbonyl, and the like; the benzoylmethylsulfonyl group, the 2-(nitro)-phenylsulfenyl group, the diphenylphosphine oxide group, and like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the t-butoxycarbonyl, and phenoxyacetyl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7.

As used herein, the term "carboxy-protecting group" refers to one of the groups commonly employed to block or protect the carboxylic acid group while reactions are carried out on other functional groups on the compound. Examples of such carboxylic acid-protecting groups include allyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenyl-prop-2-yl, trimethylsilyl, t-butyldimethylsilyl, phenacyl, 2,2,2-trichloroethyl, b-(trimethylsilyl)ethyl, b-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject the carboxy-protecting molecule to strong nucleophilic bases. Futher examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

"Under substantially anhydrous conditions" represents reaction conditions which are virtually free from water. While slight amounts of water are tolerable, the preferred condition is anhydrous.

Inert aprotic organic solvents include tetrahydrofuran, dimethylsulfoxide, dimethylpropylene urea, methylene chloride, chloroform, N,N-dimethylformamide, methyl alcohol, toluene, di- or trichloroethene, hexamethylphosphoric, triamide, dimethyl acetamide, tetrahydropyran, dioxane, acetonitrile, diethylether, dimethoxy ethane, and mixtures thereof.

The term strong base includes those bases with pKa values (of the conjugate acid) above about 15. Such bases include lithiumbis(trimethylsilyl)amide, lithium diisopropylamide, choline, Claisen's alkali, lithium amide, lithium diethylamide, lithium ethoxide, lithium hydride, lithium nitride, naphthalene sodium, phenyl lithium, phenyl potassium, phenyl sodium, potassium amide, potassium t-butoxide, potassium ethoxide, potassium hydride, potassium hydroxide, potassium-2-methyl-2-butoxide, sodium amide, sodium ethoxide, sodium hydride, sodium hydroxide, sodium t-butoxide, sodium methoxide, sodium-2-methyl-2-butoxide, sodium methylsulfinyl methide (dimsyl sodium), tetraethylammonium hydroxide, triton b, trityl lithium, trityl potassium, and trityl sodium. These bases and information thereof may be found in Ford, Gordon. "The Chemist's Companion", pp. 67–80, John Wiley and Sons, New York, N.Y. (1972).

One embodiment of the process is illustrated in the following reaction scheme:

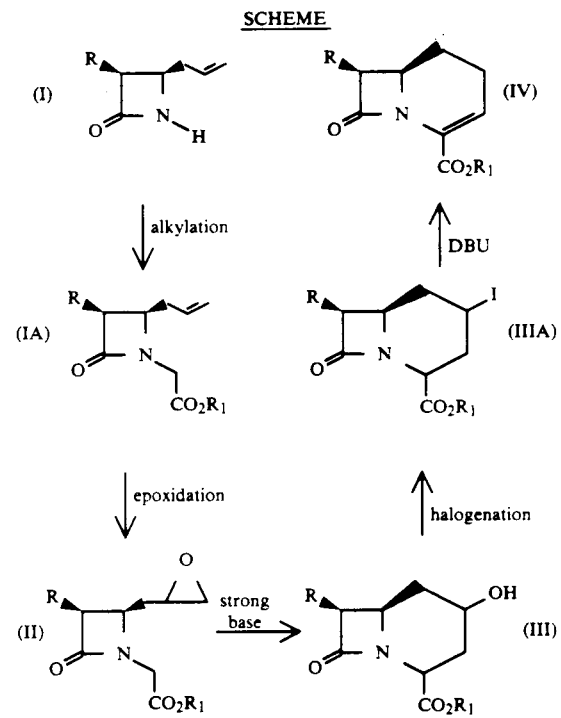

The starting material of formula (I) may be produced according to the methods described in Hall et al., U.S. patent application Ser. No. 07/410,173, U.S. Pat. No. 4,992,545, incorporated herein by reference, or as set forth in the Experimental Section.

The azetidinone (I) is alkylated to form compounds of formula (IA). The alkylation may be carried out by subjecting the azetidinone to a base such as benzyltrimethylammonium hydroxide and an alkylating agent such as tert-butylbromoacetate. The mixture is stirred at approximately 0° C., and then allowed to warm to room temperature over about 12 hours. Other methods of alkylation include those as described in March, *Advanced Organic Chemistry*, 3rd Ed., pages 422–424 (1985).

The alkylated azetidinone (IA) is then epoxidized to form compounds of the formula (II). The epoxidation may be carried out by subjecting the alkylated azetidinone in a solution of benzene to M-chloroperoxybenzoic acid. Other methods of epoxidation of the alkene portion of the alkylated azetidinone may be employed, such as those described in the March reference, pages 733 and 735–736.

The epoxidized azetidinone is then mixed with a strong base such as those previously listed. The mixing takes place at a low temperature such as between about −78° to 0° C., preferably at about 0° C., and the mixture is stirred and allowed to warm, producing a compound of formula (III). The base should be in the amount of between about 2.0 and 2.5 molar equivalents. The preferred base is lithium diisopropylamide, and in the amount of about 2.1 molar equivalents.

The compound of formula (III) is then dehydrated to form the 3-cephem compound of the formula (IV). This dehydration preferably begins by halogenating the 2-hydroxy cepham (III) at the 2-position by subjecting the compound to a halogenating agent in an amount between about 1 and 2 molar equivalents.

The term halogenating agent is defined as being a compound having an available halogen, or in other words, the compound provides a halogen. Examples of such include e.g., SbF$_5$, F$_2$, IF$_5$, BrF$_3$, SF$_4$, Cl$_2$, HOCl, (CH$_2$CO)$_2$NCl, N-chlorosuccinamide, Me$_3$COCl, NO$_2$Cl, SO$_2$Cl$_2$, Br$_2$, 1,3-dibromohydantoin, N,N-dibromobenzen-sulphonamide, HOBr, N-bromosuccinamide, C$_4$H$_8$O$_2$Br$_2$, ICl, IBR, I$_2$, N-iodosuccinamide, and 1,3-diiodo-5,5-dimethylhydantoin.

A preferred method for halogenation includes subjecting the 2-hydroxycepham to triphenylphosphine in an amount between about 1 and 2 molar equivalents, and iodine in an amount between about 1 and 2 molar equivalents in an inert organic solvent, heating the mixture at approximately 80° C. while stirring the mixture until no starting material is present, thus forming the 2-iodo cepham (IIIA).

The 2-iodocepham (IIIA) is then combined with a base such as a primary, secondary or tertiary amine base. This would include triethylamine, pyridine, diisopropylethylamine, and DBU (1,8-diazidebicyclo[5.4.0]-undec-7-ene). Preferred is DBU, and in the amount of about 1 molar equivalent. More DBU may be added and stirring continued to facilitate production of compounds of the formula (IV).

Also provided by the invention are intermediates of formula (II).

The following examples are set forth to further illustrate the invention, but are in no manner to be construed as limiting the scope thereof. The following abbreviations are used herein:
NMR = nuclear magnetic resonance spectrum;
IR = infrared spectrum;
UV = ultraviolet spectrum;
MS = mass spectrum;
OR = optical rotation.

EXPERIMENTAL SECTION

Preparation 1

(3S,4S)-3-phenoxyacetamido-4-(prop-2-ene)-4-phenylsulfonyl-1-tert-butyldimethylsilyl-2-azetidinone

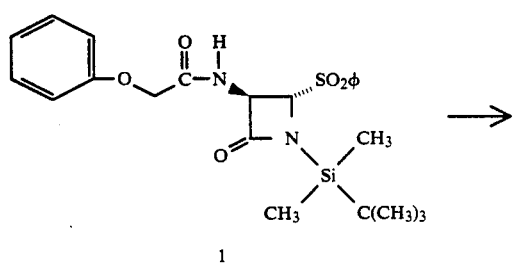

1

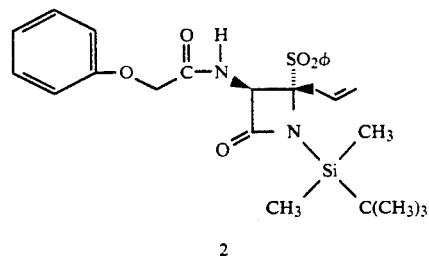

2 n-Butyllithium (49 mL of 1.6M in hexanes, 79.1 mmol) was added to a solution of compound 1 (15.0 g, 31.6 mmol) in tetrahydrofuran (100 mL) at −78° C. The reaction turned dark red during addition of the base. After 25 min, allyl bromide (4.21 g, 34.8 mmol, 3.01 mL, filtered through basic Al$_2$O$_3$) was added, the temperature was raised to −45° C., and stirring continued for 1.5 hr. The reaction was poured into EtOAc, washed 1× each with 1N HCl and brine, dried on Na$_2$SO$_4$ and concentrated. The crude product was purified by flash chromatography on silica gel (10% EtOAc/toluene to 15% EtOAc) to provide compound 2 (9.67 g, 59%): mp 94°-96.5° C.;

$^1$H NMR (300 MHZ, CDCl$_3$) δ8.60 (d, J=6 Hz, 2H), 7.78–7.58 (m, 3H), 7.26–6.94 (m, 3H), 7.10 (d, J=12 Hz, 1H), 6.64 (d, J=9 Hz, 2H), 6.26 (d, J=12 Hz, 1H), 5.80–5.64 (m, 1H), 5.31–5.24 (m, 1H), 4.95–4.86 (m, 1H), 4.36 (ABq, J=15 Hz, 2H), 3.22–3.10 (m, 1H), 2.14–2.06 (m, 1H), 1.11 (s, 9H), 0.48 (s, 3H), 0.44 (s, 3H);

IR (CHCl$_3$) 2970, 2940, 1770, 1698, 1519, 1495, 1310, 1155 cm$^{-1}$;

MS (FD) m/e 515 (M+1);

UV (EtOH) 274 nm (ε=1650), 267 nm (ε=1930), 217 nm (ε=15100);

[α]$^{25}_{365}$ +90.04° (c=0.01144, MeOH).

Elemental Analysis Calcd for: Theory: C, 60.67; H, 6.66; N, 5.44. Found: C, 60.96; H, 6.84; N, 5.45.

Preparation 2

(3S,4S)-3-phenoxyacetamido-4-(prop-2-ene)-4-phenylsulfonyl-2-azetidinone

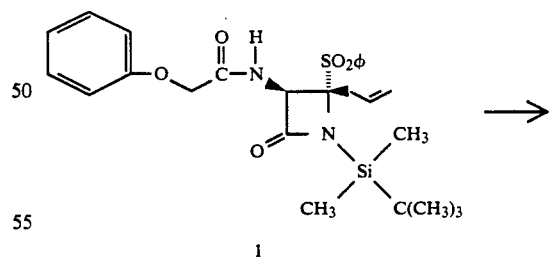

1

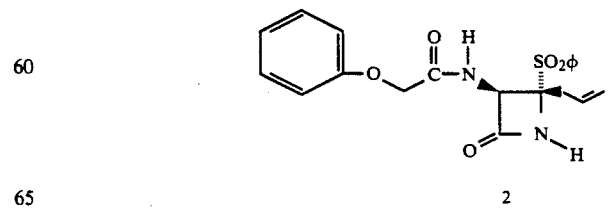

2

A solution of compound 1 (6.74 g, 13.1 mmol) in tetrahydrofuran (175 mL) was treated with 1N HCl (100 mL) and stirred at room temperature overnight. The reaction was poured into CH$_2$Cl$_2$, washed 1× each with H$_2$O and brine, dried on Na$_2$SO$_4$ and concentrated. The crude product was purified by triturating in Et$_2$O to provide compound 2 (4.02 g, 76%) as a white solid: mp 165°–168° C. (d);

$^1$H NMR (300 MHZ, CDCl$_3$+3 drops DMSO-d$_6$) δ8.94 (s, 1H), 7.98–7.50 (m, 6H), 7.19–6.72 (m, 5H), 5.87–5.71 (m, 1H), 5.61 (d, J=9.85 Hz, 1H), 5.12 (d, J=10.23 Hz, 1H), 4.99 (d, J=17.74 Hz, 1H), 4.39 (s, 2H), 2.70–2.63 (m, 1H), 2.48–2.40 (m, 1H);

IR (KBr) 3306.4, 3184.9, 3123.1, 1776.7, 1667.7, 1540.4, 1496.9, 1324.3, 1229.8, 1150.7 cm$^{-1}$;

MS (FAB) m/e 400 (M+), 258 (M+−142);

UV (EtOH) 267.8 nm (ε=2338.50), 217.4 nm (ε=17934.94), 202.4 nm, (ε=20144.33);

[α]$^{25}_{365}$+176.00° (c=0.00500, DMSO).

Elemental Analysis Calcd for: Theory: C, 59.99; H, 5.03; N, 7.00. Found: C, 60.10; H, 5.01; N, 6.75.

Preparation 3

(3S, 4R)-3-phenoxyacetamido-4-(prop-2-ene)-2-azetidinone

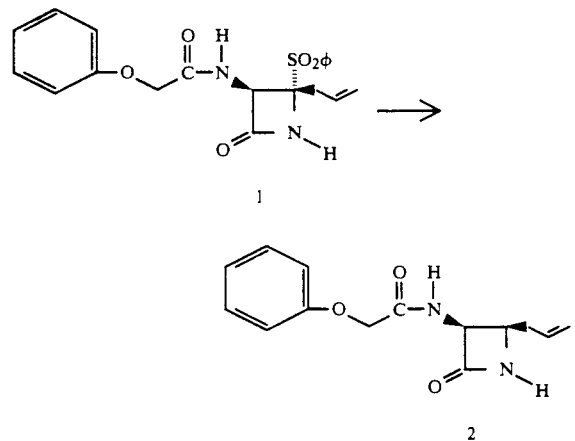

A solution of compound 1 (2.81 g, 7.02 mmol) in tetrahydrofuran (50 mL) was treated with lithium tri-tert-butoxyaluminohydride (3.97 g, 15.4 mmol) at 0° C. and stirred for 30 min. The ice bath was removed and stirring was continued for another 1.5 hr. The reaction was poured into EtOAc, washed 2× with 1N HCl, 1× with brine, dried on Na$_2$SO$_4$ and concentrated. The crude product was purified by triturating with a 1:1 mixture of Et$_2$O and EtOAc to provide compound 2 (423 mg). The filtrate was further purified by flash chromatography on silica gel (20% hexanes/EtOAc) to provide compound 2 (501 mg) as a white solid (total 924 mg, 50%): mp 142°–144° C.;

$^1$H NMR (300 MHZ, CDCl$_3$) δ7.38–6.89 (m, 6H), 6.10 (s, 1H), 5.79–5.64 (m, 1H), 5.41–5.33 (m, 1H), 5.17–5.04 (m, 2H), 4.54 (s, 2H), 4.00–3.92 (m, 1H), 2.39–2.28 (m, 1H), 2.18–2.04 (m, 1H);

IR (CHCl$_3$) 3023, 1773, 1688, 1600, 1524, 1496, 1237 cm$^{-1}$;

MS (FD) m/e 260 (M+);

UV (EtOH) 275 nm (ε=1180), 269 nm (ε=1430);

[α]$^{25}_{365}$+263.97° (c=0.01038, DMSO). Elemental Analysis Calcd for: Theory: C, 64.60; H, 6.20; N, 10.76. Found: C, 64.83; H, 6.16; N, 11.00.

EXAMPLE 1

(3S, 4R)-3-phenoxyacetamido-4-(prop-2-ene)-1-tert-butylacetate-2-azetidinone

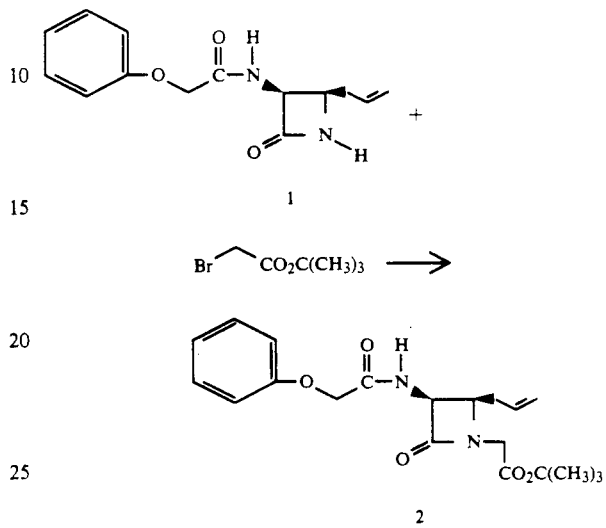

Benzyltrimethylammonium hydroxide (790 mg, 4.73 mmol, 2.15 mL of 40% solution in MeOH) was added to a solution of compound 1 (1.12 g, 4.30 mmol) and tert-butyl bromoacetate (1.05 g 5.38 mmol, 0.87 mL) in dimethylformamide (30 mL. flask not specially dried) at 0° C. and stirred overnight, allowing bath to warm to R.T. The reaction was poured into EtOAc, washed 1× with 1 N HCl, 3×with H$_2$O, 1× with brine, dried on Na$_2$SO$_4$, filtered and concentrated. The crude product was purified by flash chromatography on silica gel (50% EtOAc/hexanes) to provide compound 2 (1.45 g, 90%) as a clear, light yellow oil:

$^1$H NMR (300 MHZ, CDCl$_3$) δ7.33–6.89 (m, 5H), 7.21 (d, J=9 Hz, 1H), 5.80–5.65 (m, 1H), 5.41 (dd, J=9 Hz, 1H, 9 Hz), 5.13–5.06 (m, 2H), 4.50 (s, 2H), 4.16–4.10 (m, 1H), 3.90 (ABq, J=18 Hz, 2H), 2.30–2.26 (m, 2H), 1.45 (s, 9H);

IR (FILM) 2979.4, 1763.2, 1741, 1685, 1532.6, 1496, 1368.7, 1230.7, 1155.5 cm$^{-1}$;

MS (FAB) m/e 375 (M+1), 319 (M+1-57);

HRMS (FAB) m/e (M+1) calcd 375.1919, obs 375.1909;

UV (EtOH) 275.8 nm (ε=1122.7), 269.0 nm (ε=1356.7), 201.6 nm(ε=15011.7);

[α]$^{25}_{365}$+63.00° (c=0.0100, DMSO).

EXAMPLE 2

(3S, 4R)-3-phenoxyacetamido-4-(2,3-epoxypropane)-1-tert-butylacetate-2-azetidinone

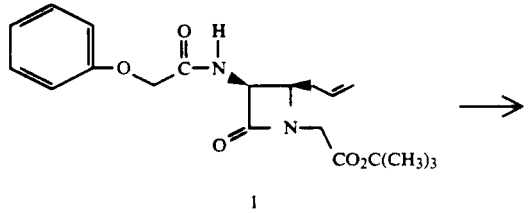

-continued

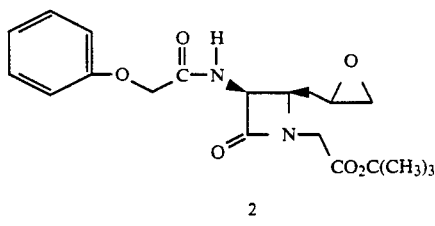

2

A solution of compound 1 (2.35 g, 6.27 mmol) in benzene (80 mL, flask not specially dried) was treated with m-chloroperoxybenzoic acid (3.25 g of 50% reagent in 60 mL benzene. 9.41 mmol, dried over $Na_2SO_4$ immediately prior to use) and refluxed for 2 hr. The reaction was cooled, diluted with EtOAc, washed 1× each with 0.1N sodium thiosulfate, saturated $NaHCO_3$ and brine, dried on $Na_2SO_4$, filtered and concentrated. The crude product was purified by flash chromatography on silica gel (45% hexanes/EtOAc) to provide compound 2 (2.10 g, 86%) as a clear oil:

$^1$H NMR (300 MHZ, $CDCl_3$) δ7.70–7.50 (m, 1H), 7.38–6.90 (m, 5H), 5.46–5.38 (m, 1H), 4.54 (s, 2H), 4.36–3.76 (m, 3H), 2.95–2.86 (m, 1H), 2.80–2.71 (m, 1H), 2.55–2.39 (m, 1H), 2.18–1.70 (m, 2H), 1.47 (s, 9H);

IR ($CHCl_3$) 3419, 2984, 1765. 1738, 1690, 1236, 1225 $cm^{-1}$;

MS (EI) m/e 391 (M+1);

HRMS (FAB) m/e (M+1) calcd 391.1869, obs 391.1879;

UV (EtOH) 275 nm (ε=1050), 268 nm (ε=1260);

$[α]^{25}_{365}$+65.30° (c=0.00536, DMSO).

EXAMPLE 3 tert-butyl (6R, 7S)-7-(phenoxyacetamido)-1-carba-1-dethia-2-hydroxycepham-4-carboxylate (2)

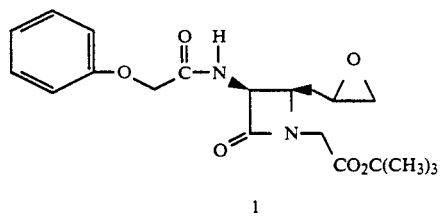

A solution of compound 1 (2.10 g, 5.38 mmol) in tetrahydrofuran (30 mL) was treated with lithium bis(-trimethylsilyl)amide (10.8 mL of 1M solution in tetrahydrofuran, 10.8 mmol) at 0° C. and stirred for 45 min. The ice bath was removed and stirring was continued for another 2.75 hr, with formation of a precipitate. The reaction was poured into EtOAc, washed 1× each with 1N HCl and brine, dried on $Na_2SO_4$, filtered and concentrated. The crude product was purified by flash chromatography on silica gel (75% EtOAc/hexanes to 85% EtOAc) to provide compound 2 (430 mg. 20%) as a fluffy white solid: mp 175°–177° C.;

$^1$H NMR (300 MHZ, $CDCl_3$) δ7.61 (d, J=7.1 Hz, 1H), 7.32–6.88 (m, 5H), 5.24 (dd, J=6.7 Hz, 1H, 6.1 Hz), 4.50 (s, 2H), 3.92–3.82 (m, 1H), 3.79–3.69 (m, 2H), 2.10–1.99 (m, 3H), 1.82–1.72 (m, 1H), 1.49 (s, 9H), 1.23–1.15 (m, 1H);

IR (KBr) 3372, 3238, 2984, 1757, 1721, 1676, 1523, 1400, 1270, 1246, 1159 $cm^{-1}$;

MS (FD) m/e 390 (M+), 333 (M+ −57);

UV (EtOH) 275 nm (ε=1180), 269 nm (ε=1420);

$[α]^{25}_{365}$+325.49° (c=0.00510, DMSO).

Elemental Analysis Calcd for: Theory: C, 61.53; H, 6.71; N, 7.17. Found: C, 61.33; H, 6.74; N, 6.95.

EXAMPLE 4 tert-butyl (6R, 7S)-7-(phenoxyacetamido)-1-carba-(1-dethia)-2-iodocepham-4-carboxylate

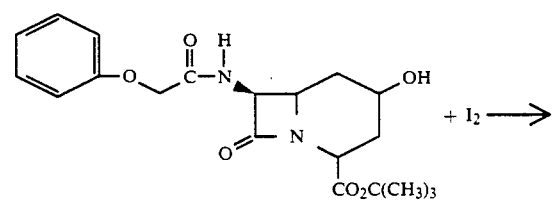

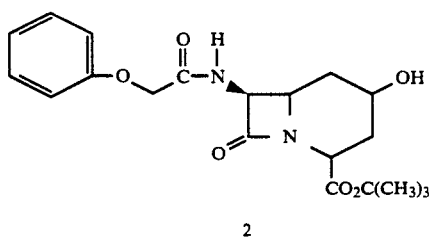

In a 100 ml round bottom flask, the starting material compound 1 (260 mg, 0.666 mmole) and triphenylphosphine (192 mg, 0.732 mmoles), were combined with toluene (15 ml), pyridine (60 μl, 0.732 mmole) and iodine (338 mg, 1.33 mmoles), and heated to 80° C. The mixture was stirred for approximately two hours. The mixture was poured into EtOAc, washed once with 1N HCl, twice with 0.1N sodium thiosulfate, and once with brine. The mixture was dried over $Na_2SO_4$, filtered and concentrated under vacuum. The product was purified by flash chromatography on silica gel (1:1 EtOAc/hexanes) to produce 86 mg of the titled product (26%).

EXAMPLE 5 tert-butyl(6R, 7S)-7-(phenoxyacetamido)-1-carba-(1-dethia)-4-carboxylate

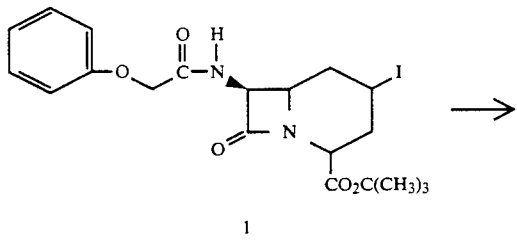

1

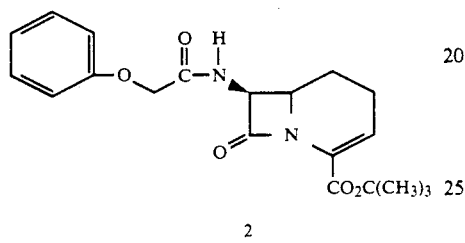

2

To a solution of the starting material (1) (134 mg, 0.268 mmol) and $CH_2Cl_2$ (5 ml) was added 1 equivalent (40 μl, 0.268 mmol) of 1,8-diazabicyclo[5.4.0]-undec-7-ene (DBU) and stirred for two hours at room temperature. Two more equivalents of DBU were added and stirred continuously for over 48 hours. The mixture was poured into EtOAc, washed with 1N HCl, and once with brine, and dried on $Na_2SO_4$, filtered and concentrated under vacuum. The product was purified by flash chromatography on silica gel eluting with 7% $EtOAc/CH_2Cl_2$ to produce 60 mg of a 70/30 $\Delta 3/\Delta 2$ mixture.

I claim:

1. A compound of the formula (II)

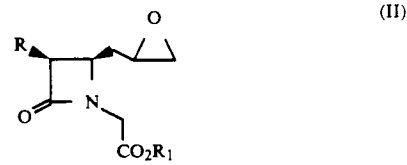

wherein R is a protected amino group and $R_1$ is a carboxy protected group.

2. The compound as recited in claim 1 wherein R is phenoxyacetamido and $R_1$ is tertiary butyl.

* * * * *